United States Patent [19]

Newman et al.

[11] Patent Number: 4,676,253

[45] Date of Patent: Jun. 30, 1987

[54] METHOD AND APPARATUS FOR NONINVASIVE DETERMINATION OF CARDIAC OUTPUT

[75] Inventors: Warren Newman, Franklin Square, N.Y.; Alfred V. Persson, Wellesley, Mass.

[73] Assignee: Doll Medical Research, Inc., Commack, N.Y.

[21] Appl. No.: 756,805

[22] Filed: Jul. 18, 1985

[51] Int. Cl.⁴ .............................................. A61B 5/02
[52] U.S. Cl. .................................... 128/693; 128/663
[58] Field of Search ................................ 128/691–694, 128/713, 663

[56] References Cited

U.S. PATENT DOCUMENTS

| Re. 30,101 | 9/1979 | Kubicek et al. | 128/713 |
|---|---|---|---|
| 3,430,625 | 3/1969 | McLeod, Jr. | 128/663 |
| 3,734,086 | 5/1973 | Phelps, Jr. | 128/2.06 R |
| 3,742,936 | 7/1973 | Blank et al. | 128/713 |
| 3,759,247 | 9/1973 | Doll et al. | 128/2.05 F |
| 3,823,706 | 7/1974 | Davis | 128/691 |
| 3,835,839 | 9/1974 | Brown | 128/2.05 V |
| 3,996,925 | 12/1976 | Djordjevich | 128/2.05 V |
| 4,134,396 | 1/1979 | Doll | 128/691 |
| 4,137,910 | 2/1979 | Murphy | 128/2.05 R |
| 4,258,720 | 3/1981 | Flowers | 128/694 |
| 4,324,258 | 4/1982 | Huebscher | 128/663 |
| 4,326,539 | 4/1982 | Obermajer | 128/713 |
| 4,425,920 | 1/1984 | Bourland et al. | 128/672 |
| 4,437,469 | 3/1984 | Djordjevich et al. | 128/672 |
| 4,450,527 | 5/1984 | Sramek | 364/415 |
| 4,452,252 | 6/1984 | Saekner | 128/694 |

Primary Examiner—William E. Kamm
Attorney, Agent, or Firm—Kenyon & Kenyon

[57] ABSTRACT

A determination of cardiac output of a living being is obtained noninvasively from measurements of heart rate and pulse timing points from a blood flow waveform in relation to the "R" line from a corresponding ECG signal. The blood flow waveform may be obtained indirectly, by differentiating the output of a plethysmograph or an instantaneous blood pressure sensor or by integrating the output of a doppler sensor, or indirectly from a magnetic flowmeter, for example. Heart rate and an "R" line trigger signal may be obtained from an electrocardiogram signal. Experimentally obtained heart rate and pulse timing data were compared with invasively measured cardiac output and were processed by regression analysis to yield an equation correlation of 0.73.

14 Claims, 6 Drawing Figures

METHOD AND APPARATUS FOR NONINVASIVE DETERMINATION OF CARDIAC OUTPUT

BACKGROUND OF THE INVENTION

The present invention relates to the determination of cardiac output in a living being and, more particularly, to a method and apparatus for continuously determining noninvasively the cardiac output of an individual as a function of other heart and blood flow parameters.

One of the most important indicators of the status of the cardiovascular system of a patient is the cardiac output (the volume of blood pumped by the heart during a given period of time). Currently, information on this parameter is obtained reliably by invasive devices such as Swan-Ganz catheters. Because of the high cost and risks associated with these catheters, as well as the discomfort and trauma of invasive devices, they are useful only in seriously ill patients or patients with conditions that have potential for serious complications.

There is a growing need to obtain the same or equivalent information by noninvasive means. It would be particularly helpful if this information could be obtained continuously on a real time basis or by repetitive short measuring periods at predetermined intervals such as once a month or once a week.

Various noninvasive techniques have been proposed starting with Nyboer's pioneering work with a plethysmograph to determine stroke volume (amount of blood pumped by the heart during each contraction) from cardiovascular impedance change during a systolic downstroke (see Nyboer, J., Electrical Impedance Plethysmography, 1954, Charles C. Thomas, Springfield, IL, Publisher). Such techniques are disclosed, for example, in U.S. Pat. Nos. 4,450,527 of Sramek; No. Re 30,101 of Kubicek et al.; and No. 3,996,925 of Djordjevich. Both Sramek and Kubicek et al. measure impedance change in the thoracic region by means of a plethysmograph. Djordjevich uses a plethysmograph either on the trunk or on a limb.

In U.S. Pat. No. 4,437,469 of Djordjevich et al., plethysmographic apparatus for measuring thoracic impedance is combined with apparatus for measuring instantaneous blood pressure in a limb to determine, through mathematical manipulation of simultaneous values of these two measurements, stroke volume and cardiac output, as well as other hemodynamic characteristics. The outputs from the plethysmograph and the blood pressure sensor are delivered to a processor having electronic processing units capable of modifying the impedance or blood pressure signals by addition, subtraction, multiplication, division, differentiation, integration, or exponentiation. The processor performs these manipulations to solve a set of simultaneous equations based on a mechanical and electrical model of a section of a living body.

The method of Djordjevich et al. using a combination of electrical impedance and blood pressure measurements, as well as the other above-mentioned methods using electrical impedance measurements alone, are based on mathematical models of a complex physiological system. These models necessarily incorporate many simplifying assumptions. Depending upon the divergence of an actual living body from the assumed conditions of the model, the accuracy of these methods can be degraded significantly. Thus, these prior noninvasive methods require great skill in application, and there still remains a need for a noninvasive technique that simply and easily determines cardiac output.

SUMMARY OF THE INVENTION

The present invention results from the discovery that there is a strong correlation between the cardiac output of a living being and the heart rate and various timing parameters of a blood flow pulse waveform.

The principal object of the present invention is to provide a simple and easy method and corresponding apparatus for obtaining noninvasively a measurement of cardiac output.

Another object of the invention is to provide a noninvasive method and apparatus for determining cardiac output based on maximizing the correlation between readily measured hemodynamic timing parameters and directly measured cardiac output.

The method of the invention comprises:
sensing a series of electrocardiac first signals sensed at a first location on the skin surface of the living being adjacent to the heart for use as a series of synchronizing and timing signals;
sensing a series of second signals sensed at a second location on the skin surface of the living being that are related to instantaneous blood flow;
processing the first series of first signals to obtain an average value of heart rate;
processing the second signals to obtain a blood flow waveform signal corresponding to instantaneous blood flow at the second location;
measuring the time from the "R" line of each ECG signal to a predetermined point on the corresponding blood flow waveform signal to determine at least one corresponding pulse timing delay signal; and
processing the average heart rate value and the pulse timing delay value to obtain a final value representing the cardiac index of the living being. This cardiac index is multiplied by the body surface area (BSA) of the particular living being tested to arrive at cardiac output.

The corresponding apparatus of the invention comprises:
means for sensing a series of electrocardiac first signals sensed on the skin surface of the living being;
means for sensing a series of second signals sensed on the skin surface of the living being, the series of second signals related to instantaneous blood flow;
means for processing the series of first signals to obtain an average heart rate value determined from the "R" line of each electrocardiac wave;
means for processing the series of second signals to obtain a blood flow waveform signal;
means for measuring the time from each "R" line signal to at least one predetermined point on the corresponding blood flow waveform signal to obtain at least one corresponding pulse timing delay value; and
means for processing the average heart rate value and the pulse timing delay value to obtain a final value representing the cardiac index of the living being.

The specific features and advantages of the invention will be explained in connection with the accompanying drawings.

DETAILED DESCRIPTION OF THE PREFERRED EMBODIMENT

Figure 1A:
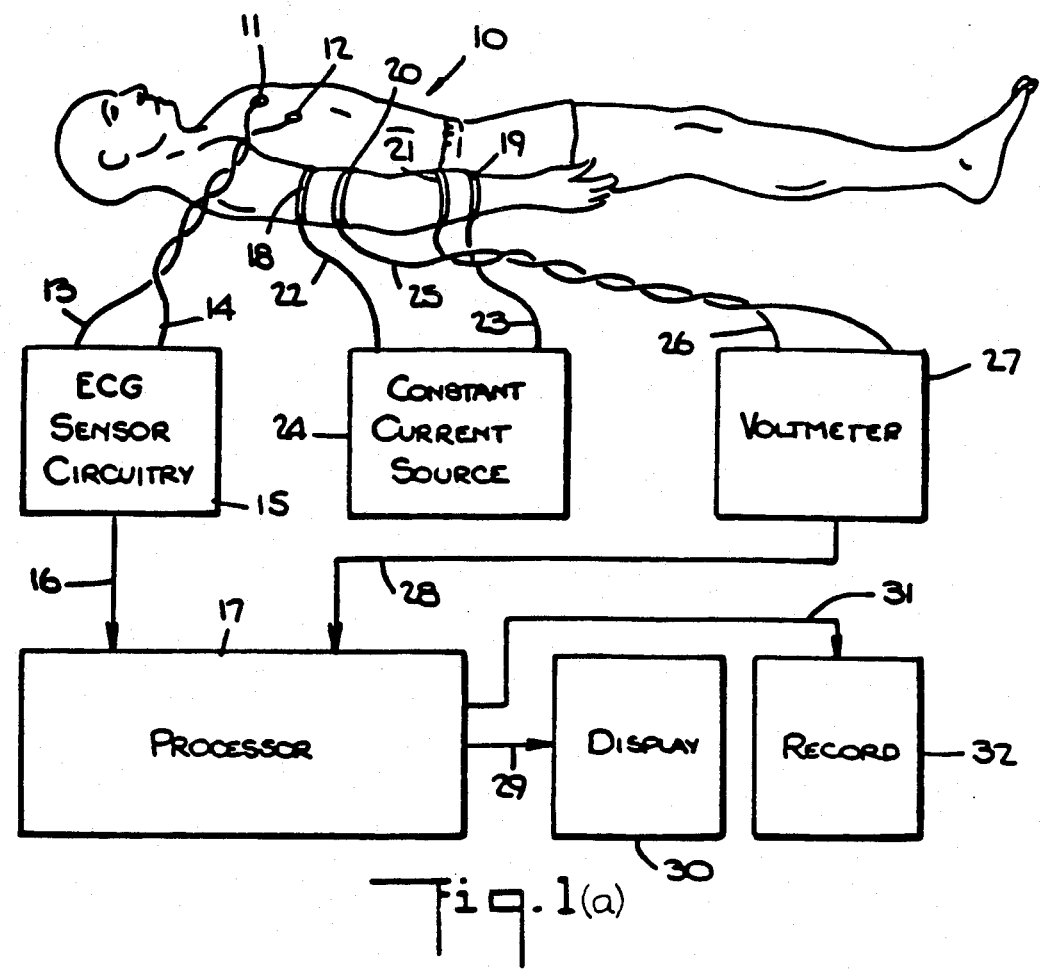
FIG. 1(*a*) is a block diagram of a preferred embodiment of apparatus for noninvasively determining the cardiac output of a living being, showing an impedance plethysmograph means of sensing a second signal.
FIG. 1(b) is a block diagram of an embodiment showing a doppler flowmeter device means of sensing a second signal.
FIG. 1(c) is a block diagram of an embodiment showing a non-invasive electro-magnetic flowmeter means of sensing a second signal.
FIG. 1(d) is a block diagram of an embodiment showing a strain gage means of sensing a second signal.
Figure 1B:
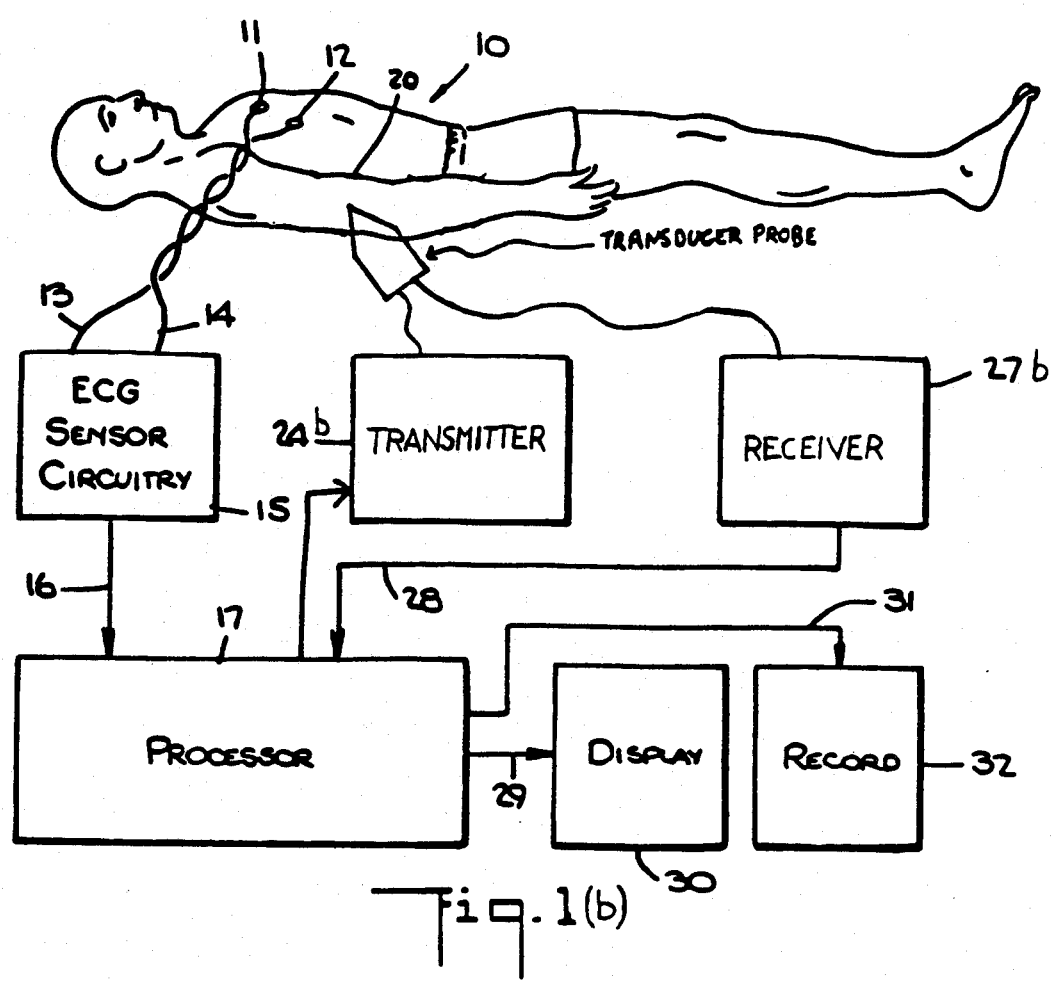
Figure 1C:
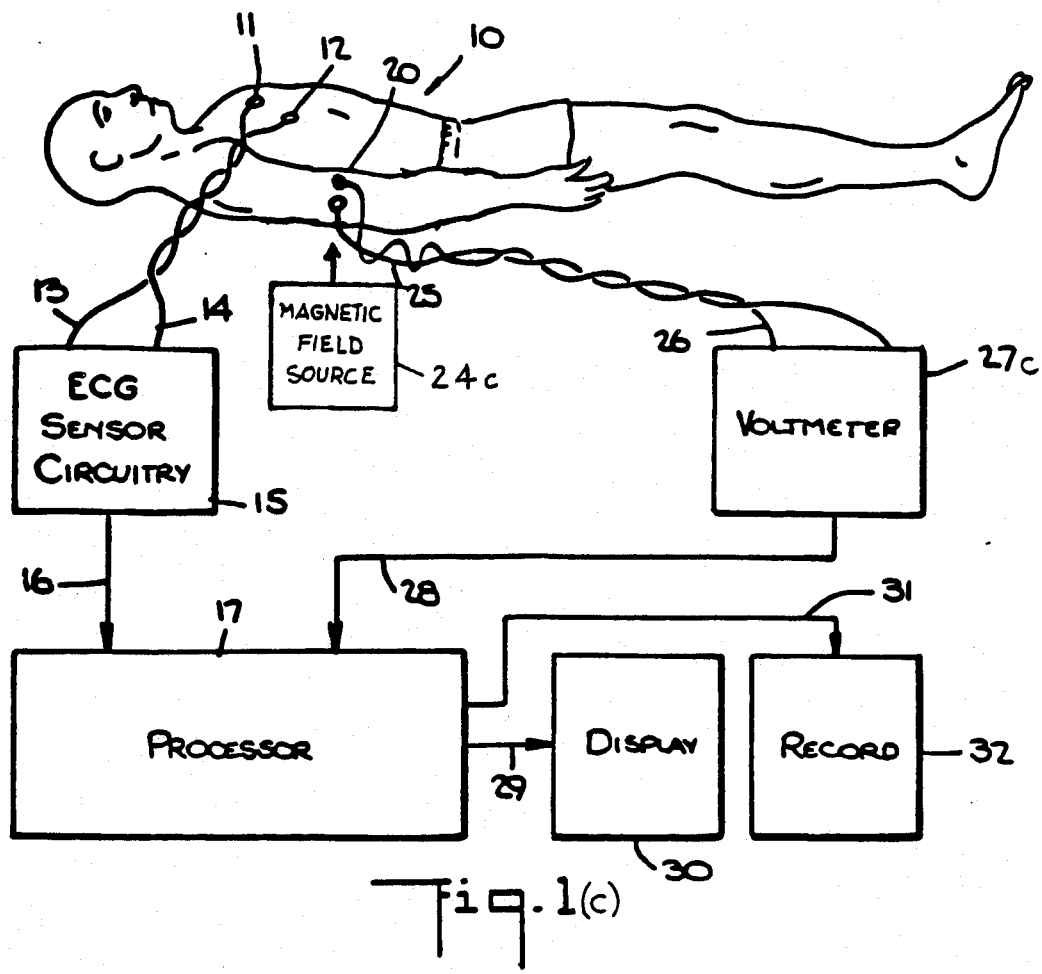
Figure 1D:
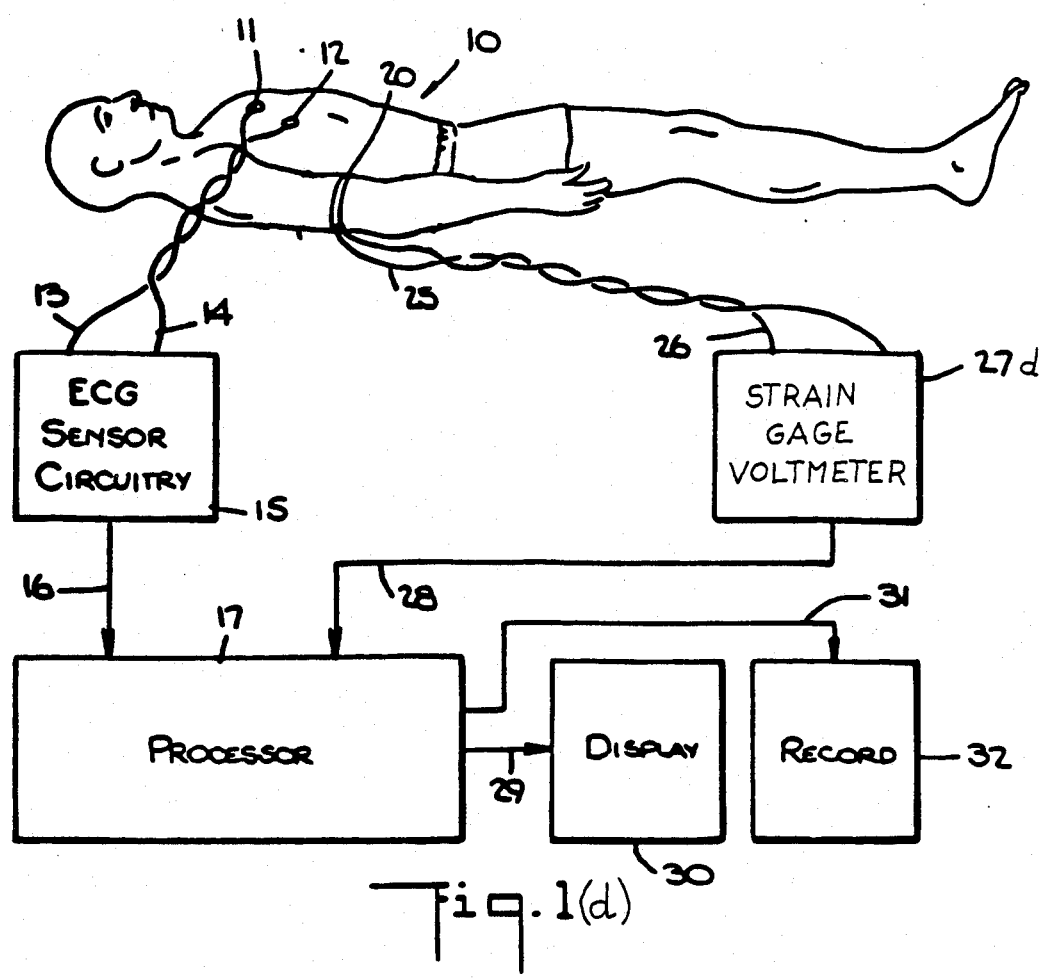

With reference to FIG. 1(a), two sets of electrical sensors are applied to obtain the signals used by the present invention to determine the cardiac output of the patient. The first set of sensors, electrodes 11 and 12, are placed at a first location on the chest of the patient in the standard position for obtaining a strong ECG signal. This signal is delivered through twisted leads 13 and 14 to electrocardiograph (ECG) sensor circuitry 15 where the "R" line of the ECG wave for each heart cycle is shaped and clipped by conventional circuitry to become a synchronizing and timing pulse for the system. This synchronizing and timing pulse is delivered via line 16 to a processor unit 17.

The second set of sensors preferably comprises a first pair of band electrodes 18 and 19 and a second pair of band electrodes 20 and 21. These two pairs of electrodes can be spot electrodes rather than band electrodes, but the circumferential band electrodes provide more reliable signals. Both pairs of electrodes are applied to a second location on a limb of the patient, the presently preferred location being a region of the arm just below the elbow. The first pair of electrodes 18 and 19 are spaced a substantial distance apart, and the second pair of electrodes 20 and 21 are spaced apart within the first pair.

Electrodes 18 and 19 are connected via leads 22 and 23, respectively, to a constant current source of high frequency, for example, a source delivering 1 ma at 100 kHz. The frequency and amplitude of this current poses absolutely no danger to the patient. The second pair of electrodes 20 and 21 are connected via leads 25 and 26, respectively, to a voltmeter device 27. Thus, the second set of sensors, together with the current source 24 and the voltmeter 27 comprise a conventional electrical impedance plethysmograph that delivers a voltage output signal, as a result of the impressed constant current between the outer pair of electrodes, that is directly proportional to the instantaneous changes in impedance of the section between electrodes 20 and 21. This voltage output signal consequently is inversely proportional to the instantaneous changes in blood volume in this section of the limb. The voltage output signal is then delivered via line 28 to the processor 17.

Processor 17 may be any device for processing plethysmographic or similar waveform signals. The processor may be analog or digital and should contain circuits to be programmed for performing mathematical functions such as waveform averaging, signal rejection, differentiation, integration, addition, subtraction and multiplication. Circuits or programs for performing these functions are conventional and well known, and they form no part of the present invention. Analog to digital converters must be provided in a digital environment for digital value sampling of otherwise analog signals.

In many cases, the preferred processor may be a microcomputer programmed to accomplish the necessary synchronizing and signal processing functions and to deliver the processed information via line 29 to a display 30, such as a CRT monitor, and via line 31 to a permanent recording device 32, such as a printer and/or a plotter. A microcomputer has the advantage over dedicated analog or digital processors in that it has the flexibility to be programmed to store and analyze data and to provide hard copy in many different forms. Thus, it allows the apparatus to be used for other purposes and to obtain measurements of other significant parameters.

FIG.'s 1(b), 1(c) and 1(d), show alternative apparatus where the impedance plethysmograph shown as including current source 24 and voltmeter 27 is replaced by a doppler flowmeter including transmitter 24b and receiver 27b, by a non-invasive electromagnetic flowmeter including magnetic field source 24c and voltmeter 27c, and by a strain gage voltmeter 27d, respectively.

The following table provides a detailed step-by-step algorithm comprising 17 steps for operating the apparatus of FIG. 1(a):

Table 1

Algorithm

1. Apply ECG electrodes 11, 12 to chest.

2. Apply current source and voltage sensing electrodes 18, 19, 20, 21 to arm.

3. Start the measurement process by enabling processor 17.

4. Measure the volumetric voltage signal 28 from the impedance plethysmographic channel 26, 27, which is the product of the applied current from current source 24 (whose frequency and amplitude are known) and the limb impedance.

5. The ECG signal 16 is transmitted toward processor 17.

6. The volumetric voltage and ECG signals 16 and 28 respectively are then digitized by an analog-to-digital converter operating at an appropriate sampling frequency.

7. The digitized signals are passed, for a predetermined delay period, to the processor's memory for storage prior to further processing.

8. The volumetric data is replaced with data generated by differentiating. The resulting differentiated data is representative of blood flow.

9. The ECG signals are processed to determine the occurrence of each successive "R" line. The point at which each "R" line occurs is used to mark the starting point of each heart cycle. Noise and bad data are eliminated in accordance with processes disclosed in U.S. Pat. No. 3,809,070.

10. Average heart rate is calculated by taking the inverse of the average of the intervals between the successive "R" lines on the ECG data. Noise and bad data are similarly eliminated as in step 9.

11. Using the "R" line timing points for synchronization, the digitized blood flow signals are averaged to form a composite signal.

12. The beginning of the systolic portion of the blood flow waveform (point "S" in FIG. 3) is stored as the point at which line AMX crosses the X-axis. Line AMX is calculated by fitting a straight line between the points on the ascending portion of the curve within the range of one quarter to three quarters of the peak amplitude.

13. Point "M" is determined by measuring the time between the "R" line of the ECG and the point at which the flow curve reaches its maximum value.

14. A value for "M-S" is determined by subtracting "S" from "M".

15. The resultant values for "S", "M", "M-S" and heart rate ("HR") are applied to the following predictive regression equation to determine the cardiac index:

$$SGCI = a(HR) - b(M) - c(M-S) + d$$

where SGCI is the cardiac index and a, b, c, and d are constants, the value of which being dependent on the experimental data.

16. The cardiac index value can be converted to cardiac output by multiplying the cardiac index by the patient's body surface area (BSA).

17. The cardiac index or cardiac output values may be saved on a hard copy device 32 such as a printer or displayed on display 30.

Figure 2:
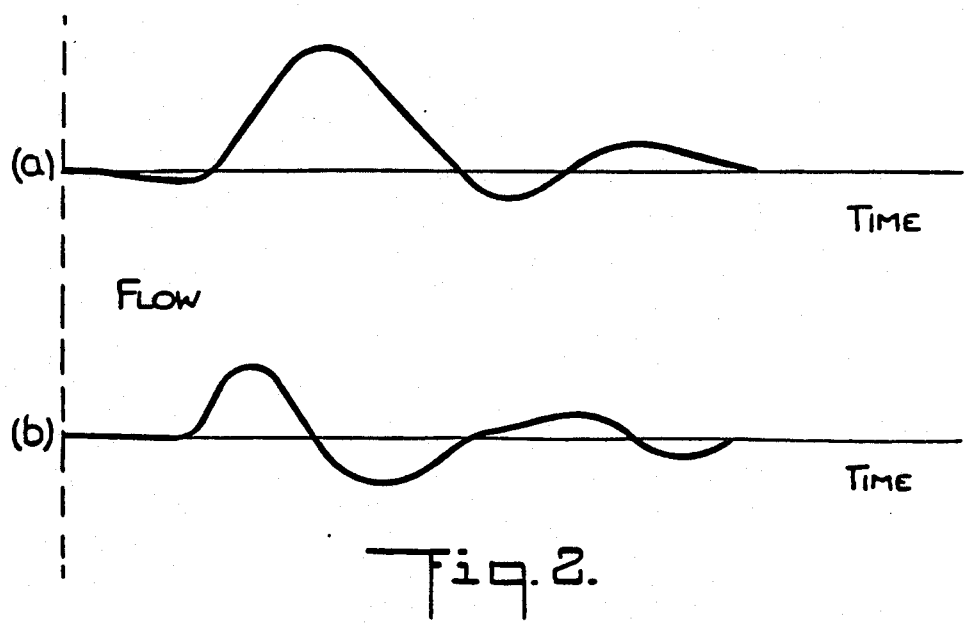
FIG. 2 presents comparative typical blood volume (waveform (a)) and blood flow (waveform (b)) waveforms plotted as a function of time for one heart cycle.

FIG. 2 illustrates typical waveforms, after processing, of the variation in blood volume (curve (a)) and the variation in blood flow (curve (b)), curve (b) being the time-differentiated version of curve (a). It will be appreciated, of course, that the waveforms provided by a plethysmograph do not provide blood volume and blood flow amplitude information directly; the vertical scale must be calibrated against some other means for obtaining these values either directly or by calculation. An important advantage of the present invention, however, is that quantitative amplitude values are not needed, since the cardiac output is determined from the relative timing of significant blood flow waveform events or parameters, not by their amplitude.

As mentioned previously, the impedance signal delivered by the sensors 20 and 21 is inversely proportional to the volume change in the limb. The first derivative of the volume signal yields a waveform that is proportional to the blood flow. The flow signal is the signal that is processed and analyzed by the device.

The flow waveform is used because it is easier to relate this waveform to real cardiovascular events. Changes in peak amplitude, area under the systolic portion of the waveform (systolic volume changes) and the acceleration of the waveform give information about the strength of contraction of the heart. Changes in transit time, amplitude, area and deceleration indicate if the limb is becoming more or less vasodilated or vasoconstricted. An additional benefit of differentiating the volume curve is that this has the effect of a first order high pass filter. This results in the removal of any offsets or low frequency ramps that may have been affecting the baseline of the volume waveform.

Figure 3:
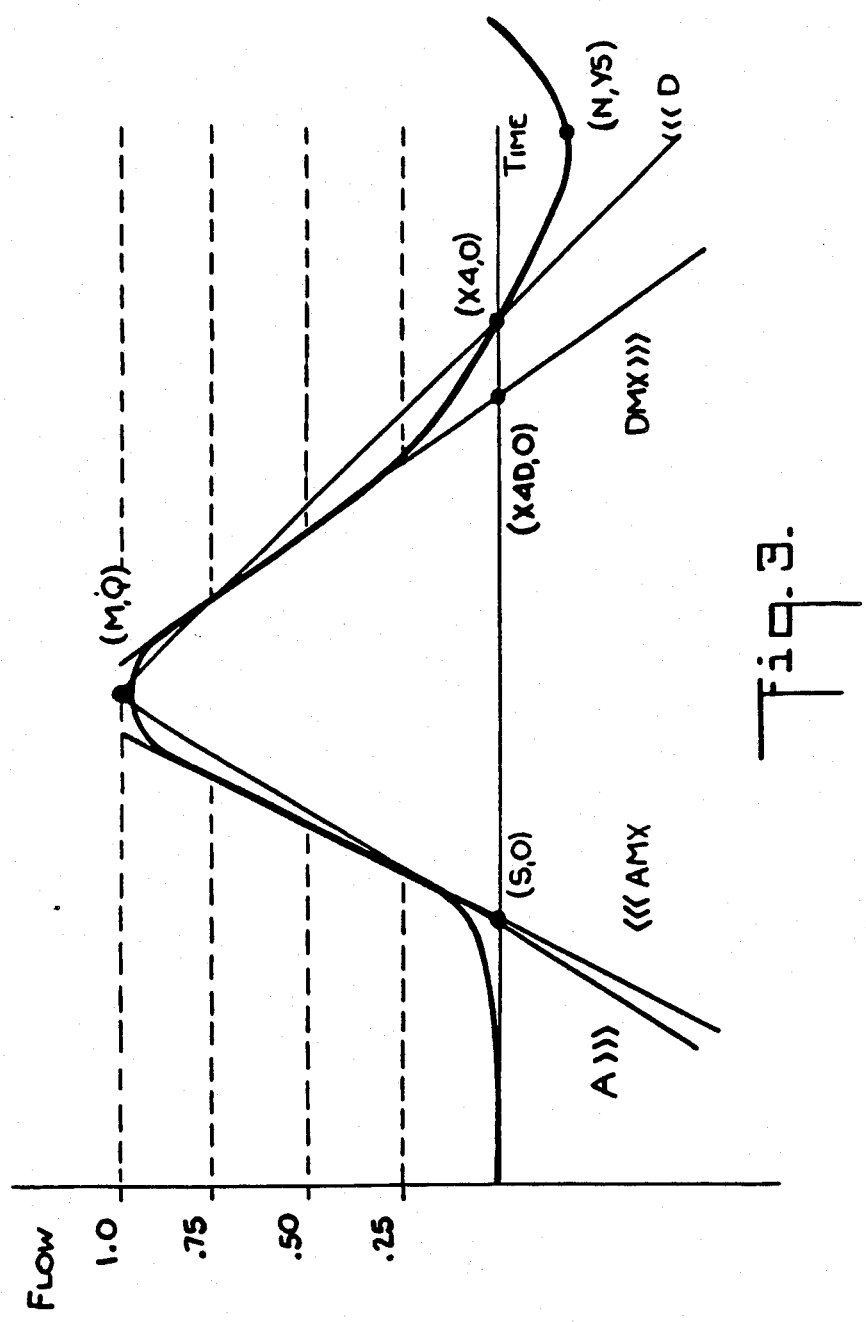
FIG. 3 presents a portion of the blood flow waveform b of FIG. 2 to an enlarged scale for illustrating significant flow parameters.

FIG. 3 illustrates the initial portion of the blood flow waveform (b) of FIG. 2 at an enlarged scale to show more clearly the several parameters of interest. The beginning of the X-axis represents the time of heart contraction as detected from the "R" line of the ECG. The parameters are defined as follows:

S: Onset of systole. This is the point at which line AMX crosses the X-axis. It represents the time that it takes for the blood flow pulse to travel from the heart (as detected by the "R" line) to the measuring site. It is also known as the "Pulse Transit Time" or the "Pulse Arrival Time".

M: Time to flow maximum. This is the time that it takes for the pulse to reach its peak as measured from the detection of the "R" line.

X4: Time to first zero crossing after flow maximum. This time represents the end of the systolic period of the flow pulse.

X4D: Time to defined end of systole. This is the point at which the line DMX intersects the X-axis. It is used as a more reliable timing mark than X4 since the flow waveform occasionally rides just above the X-axis for long periods before returning to zero.

N: Time to flow minimum. This is the time during diastole at which the flow curve reaches its most negative value.

Q: Peak flow rate. This is the value during systole when the pulsatile flow is maximum.

Y5: Minimum flow rate. This is the absolute value of the maximum displacement of the curve below the pulsatile zero line.

A: Ascending slope. This is the peak flow rate divided by the interval between the onset of systole and the time to flow maximum $[Q/(M-S)]$.

D: Descending slope. This is the peak flow rate divided by the interval between the time to flow maximum and the first successive zero crossing $[Q/(S-X4)]$.

AMX: Maximum ascending slope. This slope is calculated by fitting a straight line between the points on the ascending portion of the curve within the range of one quarter to three quarters of the peak amplitude.

DMX: Maximum descending slope. This slope is calculated by fitting a straight line between the points on the descending portion of the curve within the range of three quarters to one quarter of the peak amplitude.

As mentioned above, the present invention results from the discovery that certain timing parameters of the instantaneous blood flow waveform, in addition to the heart rate, present a strong correlation with cardiac output. This discovery resulted from statistical analyses of the correlation between the heart rate and several selected timing parameters of the blood flow waveform, on the one hand, and the cardiac output measurements obtained by conventional invasive thermodilution using a Swan-Ganz catheter, on the other hand.

Forty-eight measurements were taken on twenty-five patients. The patients had been catheterized with a Swan-Ganz catheter for various reasons not related to the test, and arrangements were made to take ECG and plethysmographic data with apparatus as illustrated in FIG. 1 simultaneously with scheduled cardiac output measurements using cold saline injections with the catheter.

The following data were developed for each set of measurements:

HR: The patient's average heart rate as calculated from the ECG signal.

S: The time between the R-line of the ECG signal and the onset of the systole, as defined above.

M: The time from the R-line pulse to the peak of the flow waveform.

XD: The time from the R-line pulse to the defined end of systole (identical to X4D as defined above in connection with FIG. 3).

M−S: The time from onset of systole to the peak of the blood flow waveform.

XD—S: The time from onset of systole to the defined end of systole.

XD—M: The time from the peak of the blood flow waveform to the defined end of systole.

SGCI: A normalized cardiac output, known as "cardiac index", equal to the Swan-Ganz cardiac output divided by the patient's body surface area (BSA).

The results of a correlation analysis of each of the above selected timing parameters with respect to the Swan-Ganz Cardiac Index, SGCI, is tabulated below:

|  | SGCI |
| --- | --- |
| HR | +0.616 |
| S | −0.328 |
| M | −0.424 |
| XD | −0.426 |
| M-S | −0.240 |
| XD-S | −0.267 |
| XD-M | −0.245 |

Not unexpectedly, heart rate, HR, shows a relatively high correlation with the SGCI. Surprisingly, however, several of the other parameters correlated well with the SGCI. Even more surprising, a linear regression analysis of various combinations of the above variables indicates that the best correlation is provided by only three factors; HR, M and M-S, with the contribution of the last factor being of minor significance. The regression analysis yields the following predictive equation:

$$SGCI = a(HR) - b(M) - c(M-S) + d$$

where a, b, c and d are constants, the value of which will depend on the experimental data. For example, the 48 measurements discussed above yielded the values:
a=0.0211;
b=0.0092;
c=0.0033;
d=2.811.

The multiple correlation provided by the equation with the test data is 0.73, indicating that selected timing parameters from the blood flow waveform in conjunction with the average heart rate can provide a satisfactory determination of cardiac index.

Another predictive equation, giving almost as good a correlation is in the form:

$$SGCI = e(HR) - f(S) + g$$

where for the same data,
e=0.0212;
f=0.0142;
g=2.9303.

It must be emphasized that the above equations are merely exemplary and represent the best correlations obtained by a linear regression analysis on a limited set of measurements. The measurements were not made under optimal research conditions, and no attempt was made to select the best data or to determine the reason for readings that departed significantly from the average value. A preliminary analysis suggests that this technique may be less accurate for patients with various types of edema, but it is believed that with refinement of data gathering techniques (including improvement in the accuracy of measuring SCGI), the accuracy and reliability of the method of the invention will be significantly increased.

In addition to obtaining larger and more carefully controlled data samples, it is probable that the predictive equation could be further improved by using more sophisticated analysis, such as geometrical regression instead of linear regression techniques.

The above results demonstrate, however, that the heart rate and selected timing parameters of the blood flow waveform can be combined through statistical analysis to provide a simple and easy method for determining the cardiac output of a living being by noninvasive means.

Although the presently preferred apparatus for determining heart rate and the R-line reference is an ECG device, and the presently preferred apparatus for generating a blood flow waveform is a plethysmograph, other apparatus can be used for obtaining these measurements.

For example, any sensor capable of sensing and discriminating the R-line of a heart pulse and of providing a reliable accurate heart rate could be substituted for the ECG electrodes. A strain gage, pressure transducer, or accelerometer might be suitable substitutes. Similarly, a doppler device, either of the ultrasonic or the laser type, could be used to generate a blood flow waveform. Since doppler devices produce a velocity signal, it would be necessary to integrate the output to obtain a waveform corresponding to blood flow.

Alternatively, an electromagnetic blood flow meter can be used to produce a blood flow waveform directly. A suitable type of electromagnetic blood flow meter is described in U.S. Pat. No. 3,809,070 of Doll et al., the disclosure of which is incorporated herein by reference both for its showing of an electromagnetic flowmeter and for its description of signal processing circuitry suitable for a processor such as processor 17 in FIG. 1. Still another possible apparatus for obtaining a blood flow waveform is a strain gage. Since the output of such a device is proportional to volume change, the output should be differentiated to provide a blood flow waveform signal.

Finally, the blood flow waveform sensor can be placed at locations other than the arm or other limb of the patient. For example, the above-mentioned doppler device could be positioned to sense flow velocity in the descending aorta. The important requirement is that the flow be sensed on the output side of the heart.

We claim:

1. A method for determining the cardiac index of a living being, the method comprising:
    sensing a series of electrocardiac first signals sensed at a first location on the skin surface of the living being adjacent to the heart for use as synchronizing and timing signals;
    sensing a series of second signals sensed at a second location on the skin surface of the living being that are related to instantaneous blood flow;
    processing the first signals to obtain an average heart rate value by averaging the durations between successive "R" lines of each electrocardiac wave;
    processing the second signals to obtain a blood flow waveform signal corresponding to instantaneous blood flow at the second location;
    measuring the time from each "R" line signal to a predetermined point on the corresponding blood flow waveform signal to determine at least one corresponding pulse delay timing value; and
    processing the average heart rate value and the pulse delay timing value to obtain a final value representing the cardiac index of the living being.

2. The method according to claim 1 wherein the step of measuring the time from each "R" line signal to at least one predetermined point on the corresponding blood flow waveform signal comprises measuring the time from each "R" line signal to the peak of the systolic pulse of the corresponding blood flow waveform signal.

3. The method according to claim 1 wherein the step of measuring the time from each "R" line signal to at least one predetermined point on the corresponding blood flow waveform signal comprises measuring the time from each "R" line signal to the onset of the systolic pulse of the corresponding blood flow waveform signal.

4. The method according to claim 1 wherein the step of sensing a second signal at a second location on the skin surface of the living being comprises sensing the instantaneous impedance changes between two sites spaced apart along the length dimension of the limb to obtain an instantaneous blood volume signal.

5. The method according to claim 4 wherein the step of processing the second signal to obtain a blood flow waveform signal comprises differentiating the instantaneous blood volume signal.

6. The method according to claim 1 wherein the step of processing the average heart rate value and the pulse delay timing value to obtain a final value representing the cardiac index comprises
multiplying the average heart rate value by a first predetermined constant value to obtain a modified average heart rate value;
multiplying the pulse delay timing value by a predetermined constant value to obtain a modified pulse delay timing value; and
adding the modified average heart rate value to the modified pulse delay timing value.

7. The method according to claim 6 wherein the second predetermined constant value is a negative number.

8. The method according to claim 7 wherein the step of processing the average heart rate value and the pulse delay timing value further comprises adding a third predetermined constant value signal to the sum of the modified average heart rate and pulse delay timing values.

9. The method according to claim 1 further comprising the step of:
measuring the time from the onset to the peak of the systolic pulse portion of each blood flow waveform signal to obtain a systolic rise time value, modifying the final value processing step as follows:
processing the systolic rise time value, the average heart rate value and the pulse delay timing value to obtain said final value representing the cardiac index of the living being.

10. Apparatus for determining the cardiac index of a living being, the apparatus comprising:
means for sensing a series of electrocardiac first signals sensed on the skin surface of the living being;
means for sensing a series of second signals on the skin surface of the living being related to instantaneous blood flow;
means for processing the first signal to obtain an average heart rate value by averaging the times between successive "R" lines of each electrocardiac wave;
means for processing the second signals to obtain a blood flow waveform signal;
means for measuring the time from each "R" line signal to at least one predetermined point on the corresponding blood flow waveform signal to obtain at least one corresponding pulse delay timing value; and
means for processing the average heart rate value and the pulse delay timing value to obtain a final value representing the cardiac index of the living being.

11. The apparatus of claim 10 wherein the means for sensing said second signal comprises a plethysmograph.

12. The apparatus of claim 10 wherein the means for sensing said second signal comprises a doppler device.

13. The apparatus of claim 10 wherein the means for sensing said second signal comprises an electromagnetic flowmeter.

14. The apparatus of claim 10 wherein the means for sensing said second signal comprises a strain gage.

* * * * *